Feb. 12, 1952 C. D. CORLISS Plant Pat. 1,073
EUONYMUS FORTUNEI PLANT
Filed March 13, 1950
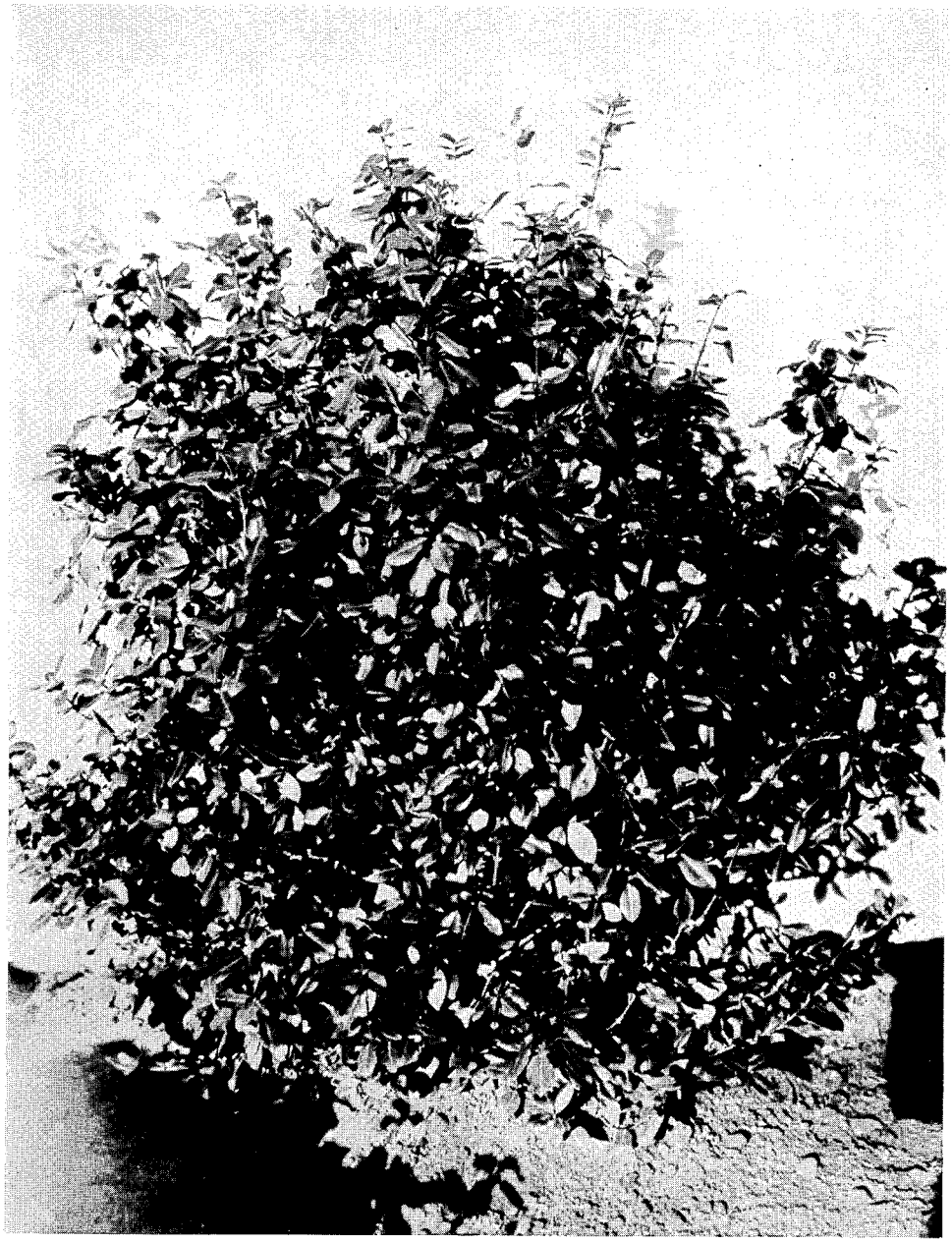
INVENTOR
Clifford D. Corliss
BY Orville M. Kile
PLANT PATENT AGENT Patented Feb. 12, 1952 Plant Pat. 1,073

UNITED STATES PATENT OFFICE 1,073

EUONYMUS FORTUNEI PLANT

Clifford D. Corliss, Gloucester, Mass., assignor to Corliss Bros., Inc., Gloucester, Mass., a corporation of Massachusetts Application March 13, 1950, Serial No. 149,245

1 Claim. (Cl. 47—59)

My present invention relates to a new and distinct variety of *Euonymus fortunei* plant which originated from a cross, made by me, between the Euonymus types *fortunei vegeta* and *fortunei radicans*.

Both parental varieties are plants of prostrate and viney growth which grow upright and in compact form only if sheared and supported. But the plant of my new variety grows entirely unsupported and without shearing, into a compact bush form which branches from one central stem with branches and branchlets resulting in an almost perfectly uniformly shaped plant.

The natural growth of the plant of this new variety is a neat, dwarf, compact, uniform shrub almost as broad as tall with heavy foliage all the way to the ground. It has an average height of 4 feet and a spread of about 3½ feet. This form is unique among Euonymus varieties and makes a plant which is very useful as a specimen shrub where dwarf or semi-dwarf evergreens are desired.

The scope of this variety's usefulness is widened because it does well in average garden soils and stands extremely dry conditions exceptionally well. Advantageous also is its great resistance to scale and other diseases—perhaps even lack of susceptibility to them since no disease has ever attacked it during the entire time that it has been grown. Its hardiness is likewise an advantage and extends the scope of its usefulness over a greater territory. It has been grown without protection where temperatures have reached as low as 20 degrees below zero and has shown no ill effects—not even a sign of winter burn which is somewhat prevalent in the parent varieties.

My new variety presents a deep green appearance, darker and more glossy than *fortunei vegeta* and with leaf texture about the same as that variety. Unlike *vegeta* and many other Euonymus varieties, the plant does not produce flowers or berries, under growing conditions so far experienced.

The root system of this new variety is fibrous and strong and the plant can be easily and successfully transplanted either with bare roots or with a good ball of earth.

Since the first production of this new variety, plants have been and are being asexually reproduced by means of cuttings at Ipswich, Massachusetts.

The accompanying illustration shows a typical plant of my new variety, particularly its compact, broad, bushy form and upright uniformly branched growth habit.

The variety most like my new variety is the subject of Plant Patent No. 881, which was likewise developed by me from the same parent combination as was used in the present case. The most outstanding points of difference are that my new variety does not produce flowers and berries, and that its spread is greater.

In the following description of growth habit, leaves and branchlets, color terminology refers to the ordinary dictionary meaning except where plate numbers are given which refer to Ridgway's Color Standards and Nomenclature.

Parentage: *Euonymus fortunei vegeta*×*Euonymus fortunei radicans*.

Growth habit: Erect shrub requiring no support or shearing. Plant grows from a central stem, forming a dense, broad evergreen shrub of neat appearance and is well bushed at the base.

Leaves: Similar to those of the *vegeta* type. Evergreen; 3 to 5 cm. long; petioles ½ to ¾ inch long; opposite; ovate to elliptical to broad ovate to suborbicular, with margins crenate-serrate revolute; apex emarginate; glossy dark-green above, between the tones of Forest Green (Pl. XVII) and Dark Dull Yellow Green (Pl. XXXII), but glossy in aspect, with dull light-green beneath approximately Biscay Green (Pl. XVII); texture similar to that of *vegeta*. Although the color is approximately as given, it is to be understood that the claim is merely to glossy, dark-green foliage as opposed to dull or light-green foliage.

Branchlets: Medium green; minutely warty. Buds elongated ovate to lanceolate; pointed. Bud-scales imbricated, lighter in color than the branchlets.

Berries: Although the original plant of this new variety is fifteen years old at the time of this application and many other plants of the variety reproduced from it are almost as old, no flowers or berries have ever appeared.

Having thus disclosed my invention, I claim:

The new and distinct variety of evergreen *Euonymus fortunei* plant, with combination of features substantially as herein shown and described, characterized particularly by its growth in upright, shapely bush form, growing from a central stem without support or shearing; its dwarf, compact, almost as broad as tall shape; the ovate to lanceolate shape of its bud; its extreme hardiness, disease resistance and ability to withstand very dry conditions; and the total absence of flowers and berries on all plants grown to date.

CLIFFORD D. CORLISS.

REFERENCES CITED

The following references are of record in the file of this patent:

UNITED STATES PATENTS

| Number | Name | Date |
|---|---|---|
| Pl. Pt. 881 | Corliss | Oct. 18, 1949 |